United States Patent [19]

Hellberg et al.

[11] Patent Number: 5,140,026
[45] Date of Patent: Aug. 18, 1992

[54] N-AMINOALKYL-S-ARYL-S-ALKYL (OR SUBSTITUTED ALKYL) SULFOXIMINES AS ANTIARRHYTHMIC AGENTS

[75] Inventors: Mark R. Hellberg, Arlington, Tex.; James R. Shanklin, Jr., Richmond, Va.

[73] Assignee: A. H. Robins Company, Incorporated, Richmond, Va.

[21] Appl. No.: 697,825

[22] Filed: May 9, 1991

[51] Int. Cl.$^5$ ................ A61K 31/415; A61K 31/535; C07C 313/00; C07D 295/108

[52] U.S. Cl. .................................. 514/238.2; 514/399; 514/608; 544/165; 544/167; 548/346; 564/101

[58] Field of Search ................ 544/165, 167; 548/346; 564/101; 514/238.2, 399, 608

[56] References Cited

FOREIGN PATENT DOCUMENTS 2920958 9/1980 Fed. Rep. of Germany .
1526996 10/1978 United Kingdom .
2011404 7/1979 United Kingdom .

*Primary Examiner*—Robert W. Ramsuer
*Attorney, Agent, or Firm*—Robert F. Boswell, Jr.

[57] ABSTRACT

Compounds of this invention are represented by the formula:

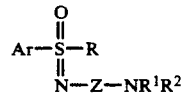

wherein Z is a $C_1$-$C_6$ alkylene group and R is an alkyl or substituted alkyl group. Class III antiarrhythmic activity is determined in vitro using an electrophysiological test where prolongation of the action potential duration is an indication of activity.

5 Claims, No Drawings

N-AMINOALKYL-S-ARYL-S-ALKYL (OR SUBSTITUTED ALKYL) SULFOXIMINES AS ANTIARRHYTHMIC AGENTS

BACKGROUND OF THE INVENTION

1. Field of Invention

This invention relates to novel N-aminoalkyl-S-aryl-S-methylsulfoximines which are useful in treating certain cardiac arrhythmias. In-vitro electrophysiological tests are indicative of class III antiarrhythmic activity with these compounds.

Several patents describe sulfoximines which are similar to compounds of this invention which are disclosed as having spasmolytic and broncholytic properties. The British patent application 2011404A discloses sulfoximines of the formula:

$$R^1-\overset{O}{\underset{N-(CH_2)_n-N}{\overset{\|}{S}}}-R^2 \quad \overset{R^3}{\underset{R^4}{\diagup}}$$

as having spasmolytic and anti-tussive properties.

In the formula, $R^1$ is phenyl, thienyl, furyl, or pyridinyl; $R^2$ is thienyl, furyl, or pyridinyl; $R^3$ and $R^4$ are loweralkyl or $R^3NR^4$ forms pyrrolidine, piperidine, or morpholine; and n is 1–5.

The Australian patent application 31,316/67 (equivalent to GB 1,168,700) discloses broncholytic and spasmolytic properties of some diphenylsulfoximine compounds having the formula:

[structure]

wherein $R^1$ is H or loweralkyl, $R^3$ and $R^4$ are alkyl, substituted alkyl, or $R^3NR^4$ forms a 5–6 membered heterocyclic ring or $R^1NR^3$ forms a 5–6 membered heterocyclic ring and n is 1 or 2.

German Auslegeschrift 2920958 and similarly Canada Patent 1,102,803 disclose Mannich bases derived from S,S-diarylsulfoximine also having spasmolytic and broncholytic utility. These compounds are represented by the formula:

[structure]

wherein $R^1$ is H or Br-, $R^3$ and $R^4$ are methyl or ethyl or $R^3NR^4$ together form the pyrrolidine, piperidine, or morpholine moiety.

The British patent 1,526,996 discloses broncholytic sulfoximines where sulfur may be substituted by groups other than aryl as shown in the following generic formula:

$$R^1-\overset{O}{\underset{N}{\overset{\|}{\underset{\|}{S}}}}-R^2 \quad \overset{R^5}{\underset{R^3\diagup\diagdown R^4}{N}}$$

where $R^1$ and $R^2$, same or different, are straight or branched chain alkyl, cycloalkyl, phenyl, naphthyl or $R^1$-S-$R^2$ forms a 5 or 6 membered ring.

The compounds shown below, Sematilide and WY-48986

[structure]

Sematilide

[structure]

WY-48986 are reported to be class III antiarrhythmic agents, unlike the structurally related class I antiarrhythmic procainamide. The only similarity between these compounds and the compounds of the present invention resides in the dialkylaminoalkylamine group.

SUMMARY OF THE INVENTION

The compounds of this invention are represented by Formula I below:

$$Ar-\overset{O}{\underset{N-Z-NR^1R^2}{\overset{\|}{\underset{\|}{S}}}}-R \quad \text{Formula I}$$

where Ar =

[structures]

$X^1 = NO_2,$ $R^1R^2NC(O)-$, $R^1SO_2N(R^2)-$, [imidazole structure],

CN, or halogen;

$X^2$ = H, $C_1$-$C_6$ alkyl, halogen, CN, or $C_1$-$C_6$ alkoxy;

R, $R^1$, $R^2$ = H (except R), $C_1$-$C_6$ alkyl or branched alkyl,

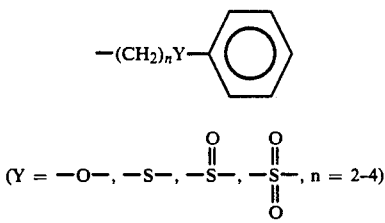

$(Y = -O-, -S-, -\overset{\overset{O}{\|}}{S}-, -\overset{\overset{O}{\|}}{\underset{\underset{O}{\|}}{S}}-, n = 2-4)$ or NR¹R² forms a heterocyclic ring of the formula:

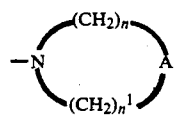

where n and n¹ are from 0–5 and n+n¹ is 3–6 and A is

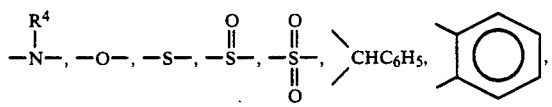

or a bond between —(CH$_2$)$_n$— and —(CH$_2$)$_n^1$—, and R⁴ is C$_1$-C$_4$ alkyl or benzyl;
and Z is C$_1$-C$_6$ alkylene.

Formula I also encompasses the geometric and optical isomers and the pharmaceutically acceptable salts which include solvates, hydrates, and pharmaceutically acceptable acid addition salts. The term pharmaceutically acceptable acid addition salt encompasses those salts formed between a basic Formula I compound and an acid recognized as pharmaceutically acceptable such as hydrochloric acid, hydrobromic acid, sulfuric acid, phosphoric acid, fumaric acid, maleic acid, succinic acid, tartaric acid, hexamic acid, methanesulfonic acid, citric acid and the like.

To further define the terms under Formula I, C$_1$-C$_6$ alkyl or branched alkyl includes methyl, ethyl, propyl, 2-propyl, butyl, sec-butyl, tert-butyl, pentyl, isopentyl, neopentyl, hexyl and the like. The term C$_1$-C$_6$ alkoxy means —O—C$_1$-C$_6$ alkyl.

The heterocyclic groups encompassed by

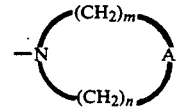

include azetidine, pyrrolidine, piperidine, piperazine, morpholine, thiomorpholine and its oxides, indoline, isoindoline and the like. The term halogen includes fluorine, chlorine, bromine, and iodine.

The Formula I compounds are evaluated for cellular electrophysiological effects in canine Purkinje fibers (in vitro) where the action potential duration is measured at 50% repolarization and 90% repolarization. Prolongation of the action potential duration is an indication of Class III antiarrhythmic activity.

DETAILED DESCRIPTION OF THE INVENTION

The formula I compounds of this invention are prepared by N-alkylation of an intermediate sulfoximine to obtain the Formula I compound directly or an intermediate N-alkylhalide which is then reacted with an amine to obtain the Formula I compound. The sulfoximines are either available commercially or prepared in several steps as outlined in the following reaction schemes.

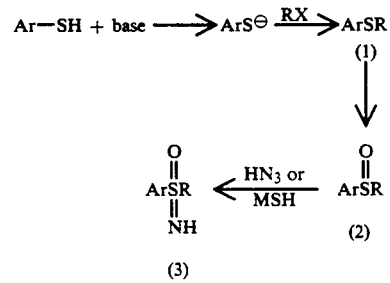

The sulfides (1) are obtained by first treating a thiol with a base such as sodium methoxide in methanol or potassium carbonate in acetone at 0° C. to 25° C. followed by addition of the appropriate alkyl halide, e.g., iodomethane, iodoethane, 2-propylbromide, 1,3-dibromopropane or 3-methylbutylbromide. The sulfides are oxidized to the sulfoxides (2) with a peroxide such as m-chloroperbenzoic acid, peracetic acid, or sodium perborate. The oxidation reaction is monitored to prevent overoxidation to the sulfone. Where m-chloroperbenzoic acid is used for the oxidation for instance, it is convenient to cool a methylene chloride solution of the sulfide to about −78° C. before adding the oxidizing agent and maintaining the reaction mixture at that temperature for a period of reaction and then allowing the temperature to rise to ambient temperature for isolation and purification procedures. Where it is desired to prepare a sulfone, oxidation with m-chloroperbenzoic acid at from ambient to reflux temperature of the solvent usually will be sufficient.

The sulfoxides are converted to the sulfoximines (3) conveniently by treating a cold (−20° C.) stirred solution of the sulfoxide and sodium azide (1.1 equivalents) in chloroform with excess concentrated sulfuric acid. After a period of reflux, the mixture is diluted with water and the organic layer separated. The aqueous layer is basified, extracted with methylene chloride, and the extract concentrated to obtain the sulfoximine. An alternative procedure is to treat the sulfoxide with o-mesitylenesulfonylhydroxylamine (MSH) according to the procedure in Synthesis, 1, 1–17 (1977).

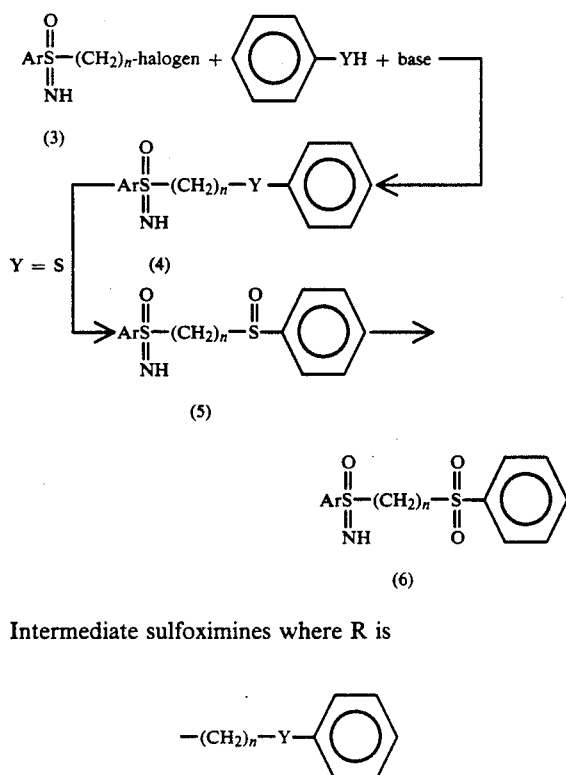

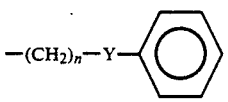

Intermediate sulfoximines where R is

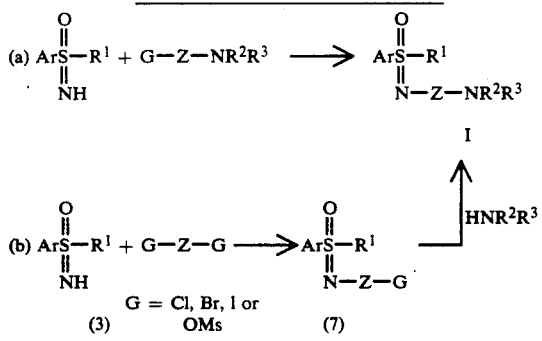

are prepared following the steps outlined in Scheme B. A S-haloalkyl sulfoximine (3) as prepared under Scheme A from a dihaloalkane is reacted with phenoxide or thiophenoxide as in Scheme A to obtain the S-aryloxyalkyl or S-arylthioalkyl sulfoximines (4). The S-arylthioalkyl sulfoximine can be oxidized as in Scheme A to obtain the corresponding sulfoxide (5) or sulfone sulfoximines (6).

Scheme C. N-substituted sulfoximines (a) ArS(=O)(=NH)—R$^1$ + G—Z—NR$^2$R$^3$ $\longrightarrow$ ArS(=O)(=N—Z—NR$^2$R$^3$)—R$^1$    I (b) ArS(=O)(=NH)—R$^1$ + G—Z—G $\longrightarrow$ ArS(=O)(=N—Z—G)—R$^1$ $\xrightarrow{HNR^2R^3}$ G = Cl, Br, I or OMs (3)  (7)

As shown in Scheme C, the Formula I compounds are prepared either in one step by alkylation following Scheme C(a) of the intermediate sulfoximine with the appropriately substituted amine following sulfoximine nitrogen anion formation by a base such as sodium hydride in a polar aprotic solvent such as dimethylformamide at from 0° C. to 50° C. for example. (Aust. J. Chem., 1986, 39, 1655-9) or two steps as shown in Scheme C(b) by reacting the sulfoximine (3) with a dihaloalkane under the same conditions as in Scheme C(a) to obtain a N-haloalkyl intermediate (7) which is reacted with an amine (HNR$^2$R$^3$) under normal N-alkylating conditions to obtain the Formula I compound. Formula I compounds thus obtained are isolated and purified using standard laboratory techniques including distillation, crystallization, chromatographic separation and salt formation.

While the foregoing methods are broadly described it is believed that one skilled in the art could carry out this invention without undue experimentation and other methods of preparation of the invention compounds will be apparent. Exact reaction conditions, isolation procedures and purification procedures will vary depending on the nature of the product, the reactants used, solvents, and other reagents employed.

Hereinbelow are given procedures for the synthesis of specific compounds of Formula I and intermediates. Intermediates or starting materials for which no preparative procedure is given are either commercially available or prepared according to published procedures. The following preparations and examples are included as illustrative of the foregoing reaction schemes and are not limiting to this disclosure in any way. The exact reaction conditions to prepare other intermediates and Formula I compounds may vary but such modifications will be apparent to one skilled in the art.

PREPARATION 1

S-(4-Bromophenyl)-S-methylsulfoximine hydrochloride

To a rapidly stirred mixture of 91.1 g (0.416 mole) of S-(p-bromophenyl)-S-methylsulfoxide and 34 g (0.520 mole) of sodium azide in 500 mL of chloroform at $-20°$ C., was slowly added 120 mL of concentrated sulfuric acid. The mixture was warmed to 25° C. and then was refluxed for 16 hr. One liter of water was added and the organic and aqueous phases were separated. The aqueous phase was extracted with several portions of chloroform and was made basic with 50% sodium hydroxide solution. The basic solution was extracted with three 400-mL portions of methylene chloride and the combined methylene chloride extracts were dried (MgSO$_4$). The methylene chloride was removed in vacuo to give 74.2 g (76.2%) of S-(p-bromophenyl)-S-methylsulfoximine as an off-white solid.

Part of this free base (11 g, 0.47 mole) was dissolved in a mixture of benzene, methylene chloride and methanol. To this solution was added an excess of ethereal HCl. The resulting white salt was collected and recrystallized from methanol-ether to give 10.56 g (0.039 mole, 83.2%) of the hydrochloride salt; mp 177° dec. The total yield was 63.4%.

Analysis: Calculated for C$_7$H$_9$NOClBrS: C, 31.07; H, 3.35; N, 5.18. Found: C, 31.38; H, 3.42; N, 5.22.

PREPARATION 2

1-[(3-Chloropropyl)thio]-4-nitrobenzene

4-Nitrothiophenol (80%, 25.0 g, 129 mmol) was added to a solution formed by adding sodium (5.55 g, 242 mmol) to methanol (500 mL) maintained at 0° C. After 0.5 h the reaction was warmed to ambient temperature and 1-bromo-3-chloropropane (50.7 g, 322 mmol) was added in one portion. The reaction mixture was stirred overnight and filtered. The filtrate was reduced to half volume and the solid which formed was collected by filtration. Recrystallization from methanol afforded 15.4 g (51%) of yellow solid, mp 50°-52° C.

Analysis: Calculated for C$_9$H$_{10}$NO$_2$Cl: C, 46.66; H, 4.35; N, 6.04. Found: C, 46.64; H, 4.28; N, 6.09.

PREPARATION 3

1-[(3-Chloropropyl)sulfinyl]-4-nitrobenzene

A solution of m-chloroperoxybenzoic acid (80%, 16.6 g, 86.3 mmol) in methylene chloride (100 mL) was added dropwise to a solution of 1-[(3-chloropropyl)thio]-4-nitrobenzene (20.0 g, 86.3 mmol) in methylene chloride (200 mL) maintained at −78° C. (dry ice/acetone bath). After 2 h the reaction was allowed to warm to ambient temperature (∼1 h) and 200 mL of 10% aqueous sodium hydroxide was added. The layers were allowed to separate and the aqueous layer was extracted (100 mL) with methylene chloride. The combined organic extracts were washed (water, 100 mL), dried (MgSO$_4$) and concentrated in vacuo. A 1.0 g sample of the residue (21.2 g) was chromatographed (Chromatatron, SiO$_2$, 4000μ, 99/1, methylene chloride:methanol) to give 0.89 g (88%) of white solid, mp 72.5°-74.5° C.

Analysis: Calculated for C$_9$H$_{10}$NO$_3$SCl: C, 43.64; H, 4.07; N, 5.66. Found: C, 43.48; H, 4.12; N, 5.63.

PREPARATION 4

2-Chloro-N-methyl-N-(2-phenylethyl)acetamide

A solution of chloroacetylchloride (10.0 g, 88.7 mmol) in tetrahydrofuran (50 mL) was added to a solution of N-methylphenethylamine (10.0 g, 73.9 mmol) and triethylamine (11.2 g, 110.8 mmol) in tetrahydrofuran (200 mL) cooled by a water/ice bath. The reaction mixture was allowed to warm to ambient temperature. After stirring for 6 h, the reaction mixture was filtered and the filtrate was concentrated in vacuo to give SiO$_2$, 1:1 ethyl acetate/hexane) to give 13.5 g (86.6%) of brown oil.

Analysis: Calculated for C$_{11}$H$_{14}$NOCl: C, 62.41; H, 6.67; N, 6.62. Found: C, 62.25; H, 6.80; N, 6.59.

PREPARATION 5

N-2-Chloroethyl)-N-methylbenzeneethanamine hydrochloride (1:1)

A solution of 2-chloro-N-methyl-N-(2-phenylethyl)acetamide (10.0 g, 47.4 mmol) in tetrahydrofuran (100 mL) was added dropwise to a stirring slurry of lithium aluminum hydride (1.80 g, 47.4 mmol) in tetrahydrofuran (50 mL) maintained at 0° C. After stirring for 3 h at 0° C., the reaction was quenched by the sequential addition of water 92 mL in 40 mL of tetrahydrofuran), 10% aqueous sodium hydroxide (3 mL) and water (5 mL). The resulting slurry was filtered through a pad of Celite. The filtrate was dried (MgSO$_4$) and concentrated in vacuo to give 6.4 g or residue. The residue was chromatographed (9:1 methylene chloride/methanol) to give 3.0 g (32.1% crude yield) of product.

A 0.30 g sample was dissolved in diethyl ether and the resulting solution was treated to ethereal HCl. A gum formed, which was converted into a solid by adding ethanol and warming the solution. The white solid that formed was collected by filtration (0.35 g, 29.6% based of the portion used), mp 114°-115° C.

Analysis: Calculated for C$_{11}$H$_{14}$NCl.HCl: C, 56.42; H, 7.32; N, 5.98. Found: C, 56.44; H, 7.57; N, 5.98.

PREPARATION 6

1-Nitro-4-[(3-phenoxypropyl)sulfinyl]benzene

A stirred solution of phenol (55 mmol) in toluene (100 mL) is treated with a solution of sodium methoxide (60 mmol) in methanol. After stirring for 30 minutes the mixture is concentrated under reduced pressure. The residue is dissolved in dimethylformamide (50 mL) and treated with a solution of 1-[3-(chloropropyl)sulfinyl]-4-nitrobenzene (50 mmol) in tetrahydrofuran (50 mL). The mixture is stirred at room temperature for 30 min and then at 50° C. for 1 hr. After cooling, the mixture is poured into water (150 mL) and the organic layer separated. The aqueous layer is extracted with methylene chloride (2×50 mL). The combined methylene chloride extract is dried (MgSO$_4$) and concentrated to obtain the title compound.

PREPARATION 7

S-(4-Nitrophenyl)-S-(3-phenoxypropyl)sulfoximine

Following the procedure of Preparation 1, the title compound is prepared from 1-[3-(phenoxypropyl)sulfinyl]-4-nitrobenzene

PREPARATION 8

4-(Methylsulfinyl)benzonitrile

A stirred solution of 4-(methylthio)benzonitrile (Aldrich Chemical Co.) (36 mmol) in methylene chloride (50 mL) at −78° C. is treated dropwise with a slurry of m-chloroperbenzoic acid (36 mmol) in 50 mL of methylene chloride over a period of 30 minutes. The mixture is stirred an additional hour at −78° C. and then allowed to warm to room temperature. The reaction mixture is washed with 3N sodium hydroxide solution (50 mL), dried (magnesium sulfate) and concentrated at reduced pressure to obtain the title compound.

PREPARATION 9

4-(S-Methylsulfonimidoyl)benzonitrile

The title compound is prepared from S-(4-cyanophenyl)-S-methylsulfoxide according to the procedure of Preparation 1.

PREPARATION 10

[(3-Chloropropyl)thio]benzene

A solution of thiophenol (55.6 g, 0.505 mol) in aqueous sodium hydroxide (22.1 g, 0.55 mole in 200 mL water) was added over a period of 30 minutes to a cold stirred solution (chilled with an ice-water bath) of 1-bromo-3-chloropropane in 100 mL of dioxanes. After the addition was complete, the ice bath was removed and the mixture stirred at ambient temperature for 4.5 h. Water was added (200 mL) and the mixture extracted with hexane (2×300 mL portions). The combined extract was washed (water), dried (MgSO$_4$) and concentrated to obtain an oil which was vacuum distilled at 85°-97° C. at 0.10 mmHg to obtain 22.38 g (89.5%) in 3 fractions.

PREPARATION 11

[(3-Chloropropyl)sulfonyl]benzene

A slurry of meta-chloroperbenzoic acid (270.3 g, 1.25 mole) in 700 mL of chloroform was stirred overnight at room temperature with chlorobutylphenylsulfide (84.26 g, 0.42 mole). The slurry was filtered and the chloroform layer was extracted with potassium carbonate and sodium bicarbonate solutions. The chloroform layer was also extracted with aqueous sodium bisulfite. The chloroform layer was dried, filtered, and solvent removed to give a white solid. A seven-gram portion of the solid was subjected to flash chromatography on silica gel using 20% ethyl acetate-hexanes and 25% ethyl acetate-hexanes for elution. Fractions from the column were combined, and the resulting oil dried in vacuo at room temperature overnight. The oil crystallized to a white solid. The process furnished 5.03 g of white crystalline product; mp 55°–58° C.

Analysis: Calculated for $C_{10}H_{13}SO_2Cl$: C, 51.61; H, 5.63. Found: C, 51.78; H, 5.64.

PREPARATION 12

1-Nitro-4-[[4-(phenylsulfonyl)butyl]sulfinyl]benzene

Following the procedures of Preparation 2, the title compound is prepared from 4-nitrothiophenol and [(4-chlorobutyl)sulfonyl]benzene.

PREPARATION 13

1-Nitro-4-[[4-(phenylsulfonyl)butyl]sulfinyl]benzene

Following the procedures of Preparation 3, the title compound is prepared from S-(4-nitrophenyl)-S-(3-benzenesulfonylbutyl)sulfide.

PREPARATION 14

4-[(4-nitrophenyl)thio]butanol

A mixture of 4-nitrothiophenol (0.11 mol), 4-chloro-1-butanol (0.09 mol), and potassium carbonate (0.1 mol) in dimethoxyethane (100 mL) is heated at reflux temperature for 18 hrs. The mixture is filtered and the filtrate is concentrated to dryness. The residue is dissolved in methylene chloride and washed with 10% sodium hydroxide. The chloroform solution is dried and concentrated to obtain the title compound.

PREPARATION 15

1-Nitro-4-[[4-(phenylmethoxy)butyl]thio]benzene

A mixture of 4-(4-nitrophenylthio)-1-butanol (10 mmol) and potassium carbonate (20 mmol) in acetone (100 mL) is treated with a solution of benzylbromide (11 mmol) in acetone (50 mL). When the addition is completed the mixture is heated at reflux temperature for 18 hrs, cooled, filtered, and the filtrate is concentrated to obtain the title compound.

PREPARATION 16

1-Nitro-4-[[4-(phenylmethoxy)butyl]sulfinyl]benzene

Following the procedure of preparation 3, the title compound is prepared from 1-nitro-4-[[4-(phenylmethoxy)butyl]thio]benzene.

PREPARATION 17

S-(4-Nitrophenyl)-S-[4-(phenylmethoxy)butyl]sulfoximine

Following the procedures of Preparation 1, the title compound is prepared from 1-nitro-4-[[4-(phenylmethoxy)butyl]sulfinyl]benzene.

PREPARATION 18

N-[2-(4-Morpholinyl)ethyl]-S-(4-nitrophenyl)-S-[4-(phenylmethoxy)butyl]sulfoximine Following the procedures used in Example 2, the title compound is prepared from 4-(2-chloroethyl)morpholine and S-(4-nitrophenyl)-S-[4-(phenylmethoxy)butyl]sulfoximine.

PREPARATION 19

4-[N-[2-(4-Morpholinyl)ethyl]-S-(4-aminophenyl)sulfonimidoyl]butanol

A solution of N-[2-(4-morpholinyl)ethyl]-S-(4-nitrophenyl)-S-[4-(phenylmethoxy)butyl]sulfoximine in ethanol is treated under nitrogen with 5% palladium on carbon catalyst and the mixture is subjected to catalytic hydrogenation on a Parr apparatus at 70° C. When hydrogen uptake ceases, the catalyst is removed by filtration and the filtrate concentrated to obtain the title compound.

PREPARATION 20

4-[N-[2-(4-morpholinyl)ethyl]-S-(4-methanesulfonylaminophenyl)-sulfoniidoyl]propanol methanesulfonate ester A solution of 4-[N-[2-(4-morpholinyl)ethyl]-S-(4-aminephenyl)sulfonimidoyl]butanol and triethylamine (3 equivalents) in methylene chloride is treated dropwise with methanesulfonylchloride (2.2 equivalents) and the mixture stirred overnight. The reaction mixture is filtered and the filtrate washed with 10% aqueous sodium bicarbonate. The methylene chloride solution is dried and concentrated to obtain the title compound.

PREPARATION 21

1-Methylsulfinyl-3,4-dichlorobenzene

Following the procedures of Preparation 3, the title compound is prepared from 3,4-dichlorothioanisole.

PREPARATION 22

S-(3,4-Dichlorophenyl)-S-methylsulfoximine

The title compound is prepared from 1-methylsulfinyl-3,4-dichlorobenzene and hydrozoic acid following the procedures of Preparation 1.

EXAMPLE 1

S-(4-Bromophenyl)-N-[2-(diethylamino)ethyl]-S-methylsulfoximine hydrate (2:1)

A solution of 4-bromophenyl-methylsulfoximine (10.0 g, 42.7 mmol) in dimethylformamide (50 mL) was added dropwise to a stirring slurry of sodium hydride (2.04 g, 51.2 mmol, 60% oil dispersion washed (3×20 mL) with hexane) which was maintained at 0° C. After stirring for 30 minutes, a solution of diethylaminoethyl chloride (6.58 g, 48.3 mmol) in dimethylformamide (20 mL) was added dropwise. The reaction mixture was warmed at 60° C. for 18 h. The reaction mixture was then cooled to ambient temperature, and 5 mL of water was added. The resulting solution was concentrated in vacuo. The residue was partitioned between 0.1N aqueous HCl (100 mL) and methylene chloride (100 mL). The layers were separated, and the aqueous layer was extracted with methylene chloride (2×50 mL). The aqueous layer was then made basic with 50% aqueous sodium hydroxide, and the resulting slurry was extracted with methylene chloride. These combined organic extracts were washed with saturated sodium chloride, dried ($Na_2SO_4$) and concentrated in vacuo. The residue was chromatographed (flash, $SiO_2$, 9:1 methylene chloride:methanol) to give 9.1 g (62%) of clear oil.

Analysis: Calculated for $C_{13}H_{21}N_2OSBr \cdot 0.5H_2O$: C, 45.62; H, 6.48; N, 8.18. Found: C, 45.66; H, 6.47; N, 8.11.

EXAMPLE 2

N-[2-(Diethylamino)ethyl]-S-[4-(1H-imidazol-1-yl)phenyl]-S-methylsulfoximine A solution of imidazole (2.05 g, 30.2 mmol) in dimethylformamide (15 mL) was added dropwise to a stirring slurry of sodium hydride (1.10 g, 28.7 mmol 60% oil dispersion, washed 3×20 mL hexane) in dimethylformamide (15 mL) maintained at 0° C. The reaction was stirred at 0° C. for 30 minutes to give a clear solution. A solution of S-(4-bromophenyl)-N-[2-(diethylamino)ethyl]-S-methylsulfoximine hydrate (2:1) (4.90 g, 15.1 mmol) in dimethylformamide (15 mL) was then added dropwise. After 30 minutes $Cu_2Br_2$ (0.39 g, 1.74 mmol) was added and the reaction mixture was warmed to 90° C. The reaction mixture was stirred at 90° C. for 18 hr before being cooled to ambient temperature. Water (5 mL) was added and the reaction mixture was concentrated in vacuo. N,N-diethylethylene diamine (2 mL) and water (100 mL) were added to the residue, and the resulting slurry was extracted with methylene chloride (3×100 mL). The combined organic extracts were washed (saturated aqueous sodium chloride), dried ($MgSO_4$), and concentrated in vacuo. The residue (4.2 g) was chromatographed (9:1:0.1, methylene chloride:methanol:concentrated ammonium hydroxide, flash, $SiO_2$) to give 1.9 g (38.2%) of S-(4-bromophenyl)-N-[2-(diethylamino)ethyl]-S-methylsulfoximine hydrate (2:1), mp 104°–105° C., as a white solid.

Analysis: Calculated for $C_{16}H_{24}N_4OS$: C, 59.97; H, 7.55; N, 17.48. Found: C, 59.34; H, 7.60; N, 17.24. Calculated for $C_{16}H_{24}N_4OS.0.25H_2O$: C, 59.14; H, 7.68; N, 17.38.

EXAMPLE 3

N-[2-(Diethylamino)ethyl]-S-methyl-S-(2-thienyl)sulfoximine

A solution of S-methyl-S-(thien-2-yl)sulfoximine (Maybridge, 2.51 g, 15.56 mmol) in dimethylformamide (15 mL) was added dropwise to a stirring slurry of sodium hydride (washed 3×20 mL hexane, 60%, 0.75 g, 18.68 mmol) in dimethylformamide (10 mL) maintained at 0° C. The reaction mixture was stirred at 0° C. for 0.5 h and then at ambient temperature for 0.5 h. The reaction mixture was cooled to 0° C. and a solution of 1-chloro-2-dimethylaminoethane (2.52 g, 18.68 mmol) in dimethylformamide (10 mL) was added. The resulting solution was warmed to 50° C. for 16 h. The reaction mixture was concentrated in vacuo. The residue was partitioned between water (40 mL) and methylene chloride (40 mL). The layers were separated and the aqueous layer was extracted with methylene chloride (2×40 mL). The combined organic extracts were dried ($MgSO_4$) and concentrated in vacuo to give a clear oil (4.0 g). The oil was chromatographed (9:1 methylene chloride/methanol, flash $SiO_2$) to give 1.60 g (38.2%) of clear oil.

Analysis: Calculated for $C_{11}H_{20}N_2OS_2$: C, 50.73; H, 7.74; N, 10.76. Found: C, 50.50; H, 8.00; N, 10.64.

EXAMPLE 4

N-[2-(Diethylamino)ethyl]-S-methyl-S-(3-thienyl)sulfoximine.

A solution of S-methyl-S-(thien-3-yl)sulfoximine (Maybridge, 2.56 g, 15.9 mmol) in dimethylformamide (15 mL) was added dropwise to a slurry of sodium hydride (0.76 g, 19.0 mmol, 60% oil dispersion, washed (3×8 mL) hexane) in dimethylformamide (10 mL) at 0° C. The solution was allowed to warm to ambient temperature and was stirred at ambient temperature for 0.5 h. The resulting mixture was cooled to 0° C. and a solution of 1-chloro-2-diethylaminoethane (2.14 g, 15.9 mmol) in dimethylformamide (15 mL) was added dropwise. The reaction mixture was stirred at ambient temperature for 15 h. Water (1 mL) was added and the reaction mixture was concentrated in vacuo. The residue was partitioned between water (25 mL) and methylene chloride (25 mL). The layers were separated and the aqueous layer was extracted with methylene chloride (2×25 mL). The combined organic extracts were washed (saturated sodium chloride), dried ($MgSO_4$), and concentrated in vacuo to afford 3.9 g of residue. The residue was chromatographed (flash, $SiO_2$, 9:1:0 to 9:1:1 methylene chloride/methanol/concentrated ammonium hydroxide) to give an oil that was partitioned between water (15 mL) and methylene chloride (15 mL). The organic layer was dried ($MgSO_4$) and concentrated in vacuo. The oil partially solidified on standing.

Analysis: Calculated for $C_{11}H_{20}N_2OS_2$: C, 50.73; H, 7.74; N, 10.76 Found: C, 50.61; H, 8.06; N, 10.69

EXAMPLE 5

S-(4-Bromophenyl)-N-[3-(diethylamino)propyl]-S-methylsulfoximine ethanedioate (1:3)

A solution of S-(4-bromophenyl)-S-methylsulfoximine (5.0 g, 21.4 mmol) in dimethylformamide (15 mL) was added dropwise to a stirring slurry of sodium hydride (60% oil dispersion, 1.3 g, 32.1 mmol; washed 3×20 mL hexane) in dimethylformamide (15 mL) cooled by a water/ice bath. The reaction mixture was warmed to ambient temperature and stirred at ambient temperature for 30 minutes. The reaction mixture was cooled to 0° C. and 1-bromo-3-chloropropane (6.7 g, 42.7 mmol) was added in one portion. The reaction mixture was warmed to ambient temperature. After stirring at ambient temperature for 2 h, the reaction mixture was warmed at 50° C. for 18 h. The reaction mixture was cooled to 0° C. and water (5 mL) was added. The resulting solution was concentrated in vacuo. The residue was chromatographed to give 4.3 g of a mixture of the desired product (65%) and the N-allyl compound (35%) (ratio by $^1HNMR$). A solution of the mixture isolated above (4.3 g) and diethylamine (3.0 g, 41.6 mmol) in acetonitrile (50 mL) was warmed at 100° C. in a stainless-steel bomb for 18 h. The mixture was cooled to ambient temperature and concentrated in vacuo. The residue was partitioned between 5% aqueous sodium hydroxide (100 mL) and methylene chloride (100 mL). The layers were separated and the aqueous layer was extracted with methylene chloride (2×50 mL). The combined extracts were dried ($MgSO_4$) and concentrated in vacuo. The residue was chromatographed (flash $SiO_2$, 9:1 methylene chloride/methanol to give 1.4 g (18.9% crude yield) of an oil.

A 0.50 g sample was dissolved in ethanol and was treated with a solution of oxalic acid in ethanol. The white solid that formed was collected by filtration to obtain 0.79 g, mp 76°–78° C.

Analysis: Calculated for $C_{14}H_{23}N_2OSBr.3C_2H_2O_4$: C, 38.91; H, 4.73; N, 4.54. Found: C, 38.95; H, 4.82; N, 4.56.

EXAMPLE 6

S-(4-Bromophenyl)-S-methyl-N-[2-[(2-phenylethyl)methylamino]ethyl]sulfoximine hydrochloride (1:2)

A solution of S-(4-bromophenyl)-S-methylsulfoximine (7.42 g, 31.7 mmol) in N,N-dimethylformamide (30 mL) was added dropwise to a stirring slurry of sodium hydride (60% oil dispersion, 1.26 g, 31.7 mmol, washed with 3×20 mL hexane) in N,N-dimethylformamide 30 mL. After the addition was complete, the reaction mixture was allowed to warm to ambient temperature and was stirred at ambient temperature for 0.5 h. The solution was cooled to 0° C. and a solution of (6.25 g, 31.7 mmol) in N,N-dimethylformamide (30 mL) was added dropwise. After the addition was complete, the reaction mixture was allowed to warm to ambient temperature. After stirring 16 h at ambient temperature, water (2 mL) was added, and the reaction mixture was concentrated in vacuo. The residue was partitioned between water (100 mL) and chloroform (100 mL). The layers were separated and the organic layer was extracted with water (2×100 mL), and the saturated sodium chloride. The organic extract was dried (MgSO$_4$) and concentrated in vacuo. The residue was chromatographed (9:1 CH$_2$Cl$_2$/MeOH, flash, SiO$_2$) to give 4.5 g (36% crude yield) of the product. A 0.5 g portion was dissolved in ethanol and was treated with ethereal HCl. The white solid that formed was collected by filtration to give 0.57 g (35% yield overall); mp 144°–45° C.

Analysis: Calc. for C$_{18}$H$_{23}$N$_2$SOBr.2HCl.0.25H$_2$O: C. 46.17; H, 5.38; N, 5.98. Found: C, 45.80; H. 5.46; N, 5.86.

EXAMPLE 7

N-[2-(4-Morpholinyl)ethyl]-S-(4-nitrophenyl)-S-(3-phenoxypropyl)sulfoximine

Following the procedures of Example 1, the title compound is prepared from S-(4-nitrophenyl)-S-(3-phenoxypropyl)sulfoximine and 4-(2-chloroethyl)morphine.

EXAMPLE 8

4-[N-[2-(4-Morpholinyl)ethyl]-S-(3-phenoxypropyl)sulfonimidoyl]benzenamine

A solution of S-(4-nitrophenyl)-S-(3-phenoxypropyl)-N-[2-(4-morpholinyl)ethyl]sulfoximine in ethanol is treated with 5% palladium on carbon catalyst and subjected to hydrogenation on a Parr apparatus. When hydrogen uptake ceases, the catalyst is removed by filtration and the filtrate is concentrated to obtain the title compound.

EXAMPLE 9

N-[4-[N-[2-(4-Morpholinyl)ethyl]-S-(3-phenoxypropyl)sulfonimidoyl]phenylmethanesulfonamide A solution of methanesulfonylchloride (11 mmol) in methylene chloride (50 ml) is added dropwise to a stirred solution of S-(4-aminophenyl)-S-(3-phenoxypropyl)-N-[2-(4-morpholinyl)ethyl]sulfoximine (10 mmol) in 50 ml of methylene chloride. After stirring for 2 hr the reaction mixture is concentrated under reduced pressure and the residue is partitioned between methylene chloride and 10% aqueous sodium bicarbonate. The methylene chloride layer is separated, dried, and concentrated to obtain the title compound.

EXAMPLE 10

4-[S-Methyl-N-[3-(1-piperidinyl)propyl]sulfonimidoyl]benzoic acid methyl ester

Following the procedure of Example 1, the title compound is prepared from S-(4-cyanophenyl)-S-methylsulfoximine and 1-(3-chloropropyl)piperidine.

EXAMPLE 11

4-[S-Methyl-N-[3-(1-piperidinyl)propyl]sulfonimidoyl]benzoic acid methyl ester

S-(4-cyanophenyl)-S-methyl-N-[3-(1-piperizinyl)propyl]sulfoximine is heated at reflux in 10% methanolic HCl to obtain the title compound.

EXAMPLE 12

4-[S-Methyl-N-[3-(1-piperidinyl)propyl]sulfonimidoyl]benzamide

Following the procedure given in *Synthetic Communications*, 20(8), 1203–1208 (1990), the title compound is obtained from the ester of Example 11.

EXAMPLE 13

N-[4-[N-[2-(4-morpholinyl)ethyl]-S-[4-(phenylthio)butyl]sulfonimidoyl]phenyl]methanesulfonamide A solution of thiophenol in toluene is added dropwise to a stirred suspension of sodium hydride (1.1 eq) in toluene. After stirring for 1 hr the mixture is heated at reflux temperature for 1 hr. After cooling to ambient temperature, a solution of S[(4-methanesulfonyloxy)butyl]-S-[4-(methanesulfonylamino)phenyl]-N-[2-(4-morpholinyl)ethyl]sulfoximine (1 eq) in toluene is added dropwise to the stirred reaction mixture. The reaction mixture is heated to reflux temperature for 18 hrs, cooled, filtered, and the filtrate washed with 10% aqueous sodium carbonate solution. The toluene solution is dried and concentrated to obtain the title compound.

EXAMPLE 14

N-[4-[N-[2-(4-morpholinyl)ethyl]-S-(4-(phenylsulfinyl)butyl]sulfonimidoyl]phenyl]methanesulfonamide A cold (0° C.) solution of S-[4-(methanesulfonylamino)phenyl]-N-[2-(4-morpholinyl)ethyl]-S-[4-(phenylthio)butyl]sulfoximine in methanol is treated slowly with excess 30% sulfuric acid and then sodium perborate tetrahydrate (10 equivalents) is added. The mixture is stirred at 0° C. for 2 hrs and then at ambient temperature for 2 hrs. The methanol is removed in vacuo and the residue basified with 50% sodium hydroxide and filtered. The filter cake is washed with methylene chloride. The aqueous filtrate is extracted with methylene chloride and the extract combined with the methylene chloride used to wash the filter cake. The methylene chloride solution is washed with water, dried and concentrated to obtain the title compound.

EXAMPLE 15

N-[4-[N-[2-(4-Morpholinyl)ethyl]-S-(4-(phenylsulfonyl)butyl]sulfonimidoyl]phenyl]methanesulfonamide The compound obtained in Example 15 is oxidized to the sulfone using the procedure of Example 15 but where the reaction is carried out at reflux temperature.

EXAMPLE 16

S-(4-Bromophenyl)-S-methyl-N-(1-pyrrolidinylmethyl)sulfoximine

Following the procedures given for the Mannich reaction in Canadian Patent 1,102,803, the title compound is prepared from S-(4-bromophenyl)-S-methylsulfoximine, pyrrolidine, and 37% formaldehyde solution.

EXAMPLE 17

S-3,4-Dichlorophenyl)-N-[2-(diethylamino)ethyl]-S-methylsulfoximine

Following the procedures of Example 1, the title compound is prepared from S-(3,4-dichlorophenyl)-S-methylsulfoximine and diethylaminoethyl chloride.

PHARMACOLOGY AND PHARMACEUTICAL COMPOSITIONS

Measurement of Cellular Electrophysiologic Effects in Canine Purkinje Fibers In Vitro Dogs (12-18 Kg) were anesthetized with sodium pentobarbital (30 mg/kg IV). The heart of each dog was rapidly removed through a right lateral thoracotomy and placed in a chilled, oxygenated Tyrode's solution. Purkinje fibers from the right and left ventricles were excised and mounted in a Lucite chamber. The tissue was superfused at a rate of 10-15 ml/min with Tyrode's solution. The temperature of the superfused Tyrode's was maintained at 37° C. and gassed with 95% oxygen-5% carbon dioxide mixture.

The Purkinje fibers were stimulated (paced at cycle length of 400 to 1000 msec) with a silver bipolar wire electrode placed on the surface of the tissue. Transmembrane action potentials were recorded with a glass capillary microelectrodes filled with 3M KCl. The action potentials were displayed on a Tectronix 5113 oscilloscope. The measurements derived from the action potential were $V_{max}$ (upstroke velocity), APD50 (action potential duration at 50% repolarization), and APD90 (action potential duration at 90% repolarization) as previously described (Bigger and Mandel, 1970; Wu and Hoffman, 1987). Test compounds were added to the reservoir of Tyrode's solution to concentrations of 10 and 100 μm. Measurements of the action potential parameters were recorded after 20 min of test drug exposure. These measurements were compared to those obtained prior to the test compound. Changes in the action potential measurements produced by the test compound were analyzed for statistical significance using a paired-t test. A minimum of 3 tissues were used for each test compound.

The compound of Example 2 increased the action potential duration at 90% repolarization by 24.7% and the action potential duration at 50% repolarization by 27.7% at a concentration of $10^{-4}$ molar. These APD values were considered significantly different from controls ($p<0.05$). The percent change in APD 90 (6.0%) and APD 50 (7.7%) at a concentration of $10^{-5}$ molar was not considered significantly different from controls ($p<0.05$).

Bigger J. T. and Mandel W. J. Effects of lidocaine on the electrophysiologic properties of ventricular muscle and Purkinje fibers. J. CLIN. INVEST. Vol 49:63-77 (1970).

Wu K. M. and Hoffman B. F. Effect of procainamide and N-acetylprocainamide on atrial flutter; studies in vivo and in vitro. CIRCULATION Vol. 76:1397-1408 (1987).

Generally, the method of treating cardiac arrhythmia in accordance with this invention comprises administering internally to warm-blooded animals, including human beings, a therapeutically effective amount of a compound of Formula I or a pharmaceutically acceptable salt in a wide variety of pharmaceutical forms well known in the art, preferably with a non-toxic pharmaceutical carrier. The active agent is administered orally, subcutaneously, intravenously, or intramuscularly and, if necessary, in repeated dosages until satisfactory response is obtained. Compositions for oral administration can take the form of elixirs, capsules, tablets, or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone. For parenteral administration, the carrier or excipient can be comprised of a sterile parenterally acceptable liquid, e.g., water or arachis oil contained in ampoules.

The effective antiarrhythmic dose of a Formula I compound in warm blooded animals is expected to be in the range of from 0.01 to 100 mg/kg and will further depend on the compound used and the route of administration.

It is only necessary that a suitable effective dosage be consistent with the dosage form employed. The exact individual dosages, as well as the daily dosages, will of course be determined according to standard medical principles under the direction of a physician or veterinarian.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention, and it is therefore understood that the invention is to be limited only by the scope of the appended claims.

What is claimed is:

1. A compound according to the formula:

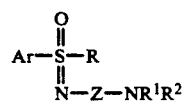

Formula I where Ar =

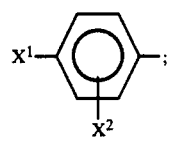

$X^1 = NO_2$,

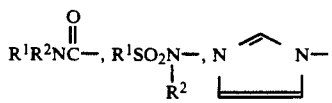

or CN;

$X^2$ = H, $C_1$-$C_6$ alkyl, halogen, —CN, or $C_1$-$C_6$ alkoxy;

R, $R^1$, $R^2$ = H (except R), $C_1$-$C_6$ alkyl or branched alkyl,

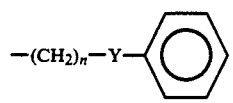

wherein Y = —O—, —S—, —S(O)—, or —S(O)$_2$— and n is 2-4 or $NR^1R^2$ forms a heterocyclic ring of the formula:

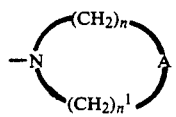

where n and $n^1$ are from 0–5 and n + $n^1$ is 3–6 and A is

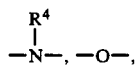

—S—, —S(O)—, —S(O)$_2$—, >CHC$_6$H$_5$,

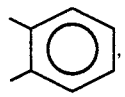

or a bond between —(CH$_2$)$_n$— and —(CH$_2$)$_n{}^1$—, and $R^4$ is H, $C_1$-$C_4$ alkyl or benzyl; Z is $C_2$-$C_6$ alkylene; or a pharmaceutically acceptable salt thereof.

2. A compound according to claim 1 which is selected from the group consisting of:
N-[2-(diethylamino)ethyl]-S-[4-(1H-imidazol-1-yl)phenyl]-S-methylsulfoximine,
N-[2-(4-morpholinyl)ethyl]-S-(4-nitrophenyl)-S-(3-phenoxypropyl)sulfoximine, or a pharmaceutically acceptable salt thereof.

3. A method of treating Class III cardiac arrhythmias by internally administering to a warm-blooded animal a therapeutically effective amount of a compound having the formula:

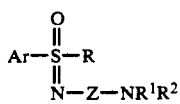

Formula I where Ar =

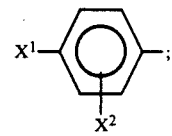

$X^1$ = NO$_2$,

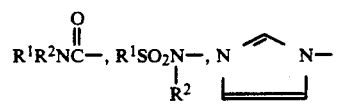

or CN, or halogen;

$X^2$ = H, $C_1$-$C_6$ alkyl, halogen, —CN, or $C_1$-$C_6$ alkoxy;

R, $R^1$, $R^2$ = H (except R), $C_1$-$C_6$ alkyl or branched alkyl,

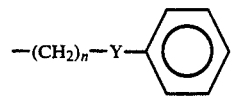

wherein Y = —O—, —S—, —S(O)—, or —S(O)$_2$— and n is 2-4 or $NR^1R^2$ forms a heterocyclic ring of the formula:

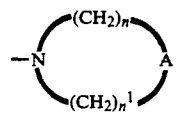

where n and $n^1$ are from 0–5 and n + $n^1$ is 3–6 and A is

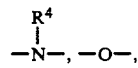

—S—, —S(O)—, —S(O)$_2$—, >CHC$_6$H$_5$,

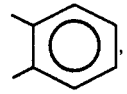

or a bond between —(CH$_2$)$_n$— and —(CH$_2$)$_n{}^1$—, and $R^4$ is H, $C_1$-$C_4$ alkyl or benzyl; Z is $C_1$-$C_6$ alkylene; or a pharmaceutically acceptable salt thereof.

4. A method of treating Class III cardiac arrhythmias by internally administering to a warm-blooded animal a therapeutically effective amount of a compound selected from the group consisting of:
N-[2-(diethylamino)ethyl]-S-[4-(1H-imidazol-1-yl)phenyl]-S-methylsulfoximine,
N-[2-(4-morpholinyl)ethyl]-S-(4-nitrophenyl)-S-(3-phenoxypropyl)sulfoximine, or a pharmaceutically acceptable salt thereof.

5. A pharmaceutical composition for the treatment of Class III cardiac arrhythmias in warm-blooded animals comprised of:
  a. a therapeutically effective amount of a compound according to the formula:

Formula 1

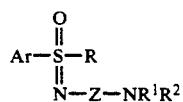

where

Ar=

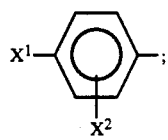

$X^1 = NO_2$,

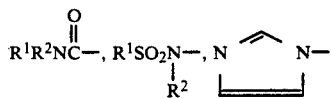

or CN, or halogen;

$X^2$ = H, $C_1$-$C_6$ alkyl, halogen, —CN, or $C_1$-$C_6$ alkoxy;

R, $R^1$, $R^2$ = H (except R), $C_1$-$C_6$ alkyl or branched alkyl,

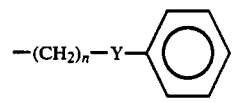

wherein Y=—O—, —S—, —S(O)—, or —S(O)$_2$— and n is 2–4 or $NR^1R^2$ forms a heterocyclic ring of the formula:

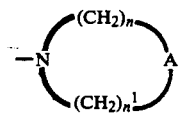

where n and $n^1$ are from 0–5 and n+$n^1$ is 3–6 and A is

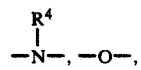

—S—, —S(O)—, —S(O)$_2$—, >CHC$_6$H$_5$,

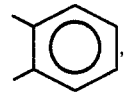

or a bond between —(CH$_2$)$_n$— and —(CH$_2$)$_{n^1}$—, and $R^4$ is H, $C_1$-$C_4$ alkyl or benzyl; Z is $C_1$-$C_6$ alkylene; or a pharmaceutically acceptable salt thereof, and b. a pharmaceutical carrier thereof.

* * * * *